United States Patent [19]

Seiler et al.

[11] Patent Number: 5,177,236
[45] Date of Patent: Jan. 5, 1993

[54] PROCESS FOR THE PREPARATION OF 3-CHLOROPROPYL-SILANES

[75] Inventors: Claus-Dietrich Seiler, Rheinfelden; Willy Hange, Wittlingen; Bernhard Lillig, Rheinfelden; Reinhard Matthes, Rheinfelden; Uwe Schön, Rheinfelden, all of Fed. Rep. of Germany

[73] Assignee: Hüls Aktiengesellschaft, Marl, Fed. Rep. of Germany

[21] Appl. No.: 893,439

[22] Filed: Jun. 4, 1992

[30] Foreign Application Priority Data

Jun. 18, 1991 [DE] Fed. Rep. of Germany ....... 4119994

[51] Int. Cl.$^5$ ................................................. C07F 7/08
[52] U.S. Cl. .................................................. 556/479
[58] Field of Search ......................................... 556/479

[56] References Cited

U.S. PATENT DOCUMENTS

| 4,292,433 | 9/1981 | Koger et al. | 556/479 |
| 4,454,331 | 6/1984 | Zeller et al. | 556/479 X |
| 4,898,961 | 2/1990 | Baila et al. | 556/479 |

Primary Examiner—Paul F. Shaver
Attorney, Agent, or Firm—Felfe & Lynch

[57] ABSTRACT 3-chloropropylsilanes are prepared from hydrogensilanes and allyl chloride, where a stoichiometric excess of allyl chloride is maintained in the condensate of the vapor emitted by the boiling reactant mixture.

2 Claims, No Drawings

PROCESS FOR THE PREPARATION OF 3-CHLOROPROPYL-SILANES

FIELD OF THE INVENTION

The present invention relates to a novel process for the platinum-catalyzed preparation of 3-chloropropyl-silanes from hydrogensilanes and allyl chloride.

BACKGROUND OF THE INVENTION

It is well known that hydrogensilanes can be reacted with allyl chloride in the presence of platinum compounds or metallic platinum, which may be present as such or applied to various substrates, to form 3-chloropropyl-silanes. Such reactions are disclosed, for example, in German Patents 20 12 229 and 28 15 316. It is further known that in the reaction of allyl chloride with hydrogensilanes to form 3-chloropropyl-silanes a portion of the allyl chloride reacts with the hydrogensilane in a so-called beta-cleavage side reaction to form propylene and the chlorosilane corresponding to the particular hydrogensilane starting compound. For instance, in the reaction of allyl chloride with trichlorosilane, about 36 mol-% of the allyl chloride involved in the reaction is converted by beta-cleavage into propylene, accompanied by the formation of equivalent amounts of silicon tetrachloride. The extent of this side reaction can be controlled only to a limited degree. By means of special reaction management in a pressure apparatus the formation of propylene can be suppressed; however, this method of operation has as its consequence that the propylene which is formed due to the beta-cleavage further reacts quantitatively to form propyl-silanes which correspond to the hydrogensilane starting compounds. Even in the reactions performed under normal pressure in conventional manner, the propylene formed due to beta-cleavage reacts to a significant degree with hydrogensilane to form the corresponding propyl-silanes. Thus, for example, in a hetero-geneous-catalytic reaction of allyl chloride and trichlorosilane on a technical scale in a column filled with platinized activated charcoal, up to 230 kg of propyltrichlorosilane are obtained per 1000 kg of 3-chloropropyltrichlorosilane, which represents an excess requirement of about 28% of trichlorosilane, based on the amount of trichlorosilane incorporated into the target product.

Whereas the chlorosilanes which are formed in stoichiometric ratio with respect to the formation of propylene due to beta-cleavage, for example silicon tetrachloride when trichlorosilane is used as the hydrogensilane component, can be easily separated by distillation from the other components of the particular reaction mixture because of the large boiling point differences, the separation of the corresponding propylsilanes from the 3-chloropropyl-silane target products is only possible with the aid of the expenditure of large distillation energy. Moreover, for most propylsilanes, such as methylpropyldichlorosilane, ethypropyldichlorosilane and dimethylpropylchlorosilane, there are at this time no fields of application, so that they require cost-intensive disposal means.

OBJECT OF THE PRESENT INVENTION

It is an object of the present invention to minimize or completely suppress the formation of propylsilanes in the synthesis of 3-chloropropyl-silanes from hydrogen-silanes and allyl chloride.

Other objects and advantages of the present invention will become apparent as the description thereof proceeds.

DESCRIPTION OF THE INVENTION

We have discovered that the above object is achieved in accordance with the present invention by heating the allyl chloride to the boiling point in a suitable vessel and passing the vapor formed thereby into a suitable cooling device in which it is condensed. The condensate is passed from the cooling device onto the platinized carrier material. The hydrogensilane is continuously added to the boiling allyl chloride at a rate which is continuously adapted to the reaction rate of the allyl chloride/hydrogensilane system, which can optionally be determined in preliminary tests, so that allyl chloride is present in stoichiometric excess, based on the hydrogensilane component, in the condensate formed in the cooling device during the entire reaction period. The molar ratio of allyl chloride to hydrogensilane is preferably at least 3:1. The result of a lesser ratio is the formation of propylsilanes to a minor extent, which are however negligible with respect to their absolute quantity, provided allyl chloride is present in stoichiometric excess in the condensate with respect to the hydrogensilane component. The addition of the hydrogensilane to the allyl chloride may also be effected discontinuously, but the hydrogen-silane portions must be reduced in correspondence to the reduction of the allyl chloride content in the vessel as the reaction proceeds.

The hydrogensilanes which may be used as starting compounds in accordance with the present invention embrace hydridosilanes and organosilanes which contain only organo groups and hydrogen atoms as substituents of the silicon., as well as organo-H-halogen- and organo-H-alkoxysilanes. An example of a hydridosilane is trichlorosilane. Examples of organo-H-halogensilanes are methylhydrogendichlorosilane, ethylhydrogendichlorosilane and dimethylhydrogenchlorosilane. Examples of organo-H-alkoxysilanes which may be used as starting compounds in the process according to the present invention, include trimethoxyhydrogensilane and methylhydrogendimethyoxysilane. Hydrogensilanes also include trimethylhydrogensilane and triethylhydrogensilane.

Preferred starting compounds are hydridosilanes such as trichlorosilane and mixed substituted hydrogensilanes wherein one of the substituents is halogen, such as methyl-, ethyl- and propyl-hydrogendichlorosilane and dimethylhydrogenchlorosilane.

The process according to the present invention can be performed under atmospheric pressure or under reduced pressure. Preferably, the process is carried out under atmospheric pressure.

The following Examples illustrate the present invention and will enable others skilled in the art to understand it more completely. It should be understood, however, that the invention is not limited solely to the particular Examples given below.

Example 1 (Comparative Example)

A 2-liter five-neck round bottom flask was placed into a heating jacket. A 20 cm long glass tube (internal diameter about 4.5 cm), which was provided with a female ground joint at its upper end with a male ground joint at its closed off lower end, was inserted into the middle of the five necks. Inside the tube above the male ground joint a glass grid was mounted on which the catalyst rested. The glass tube was also provided with two external glass tube connectors (diameter = 1 cm), namely one below the glass grid carrying the catalyst and the other below the female ground joint at its upper end. One of the five necks of the flask was connected by means of a glass tube to the upper of the two glass tube connectors of the tube containing the catalyst. Another of the five necks of the flask was connected by means of a glass tube to the straight piece of a U-tube (diameter = 1 cm); the other straight piece of the U-tube was connected by means of a glass tube with the lower glass tube connector below the glass grid. The tube containing the catalyst was connected at its upper end with an intensive cooler. The system was closed to the outside by means of a nitrogen seal. A thermometer was inserted into another of the five necks of the flask, and a dropping funnel was inserted into the last of the five necks. 150 ml of a platinized activated charcoal contact catalyst which had been run in over a longer period of time was inserted into the glass tube intended to receive the catalyst. The catalyst had a platinum content of 0.1% by weight (particle size 1 to 2 mm, bulk density 450 g/liter). The term "run in catalyst" is understood to mean a catalyst which has reached its scale plant. 4.4 mols (596 g) of trichlorosilane and 4.0 mols (306 g) of allyl chloride were introduced into the 2-liter flask by way of the dropping funnel, and a cooling solution at −32° C. was fed into the cooling device. By heating the flask, the catalyst was sprinkled from above with the starting compounds that condensed on the cooler surface. The heater output was controlled so that the system remained under a constant uniform reflux. After a reaction time of 27 hours the run was discontinued, and the sump product which had formed was analyzed by gas chromatography and worked up by distillation.

The gas chromatogram indicated the presence of 3-chloropropyl-trichlorosilane in addition to propyltrichlorosilane and unreacted allyl chloride.

The distillation of the sump product yielded 543 g of 3-chloropropyl-trichlorosilane and 109 g of propyltrichlorosilane. This corresponds to 200 g of propyltrichlorosilane, based on 1000 g of 3-chloropropyl-trichlorosilane and thus an excess consumption of 152 g of trichlorosilane per 1000 g of 3-chloropropyl-trichlorosilane.

Comparative Example 2

4.4 mols (596 g) of trichlorosilane were introduced into the 2-liter round bottom flask of the apparatus described in Example 1, and a cooling solution at −32° C. was fed into the cooler. Upon heating of the flask contents, the catalyst was contacted from above with the condensed trichlorosilane. After the beginning of vigorous condensate formation at the cooler, the heat output was controlled so that the system remained under uniform reflux. At this point of time, the addition of allyl chloride from the dropping funnel was begun. Over the course of 24 hours seven portions of 43 g each (0.57 mol) of allyl chloride were added at intervals of 4 hours. Thereafter, the reaction was allowed to go to completion by maintaining the reaction conditions for 3 hours. The sump product formed thereby was gas chromatographically analyzed and was then worked up by distillation.

The gas chromatogram showed that the sump product contained 3-chloropropyl-trichlorosilane in addition to propyltrichlorosilane and unreacted allyl chloride.

Distillation of the sump product yielded 545 g of 3-chloropropyl-trichlorosilane and 107 g of propyltrichlorosilane This corresponds to an amount of 196 g of propyltrichlorosilane, based on 1000 g of 3-chloropropyl-trichlorosilane, and thus an excess consumption of 149 g of trichlorosilane per 1000 g of 3-chloropropyl-trichlorosilane.

Comparative Example 3

The run described in Example 1 was repeated, except that 4.8 mols (650 g) of trichlorosilane and 4.0 mols (306 g) of allyl chloride were used.

The gas chromatogram of the sump product showed that it contained 3-chloropropyl-trichlorosilane besides propyltrichlorosilane and trichlorosilane. The presence of allyl chloride was not detected.

Distillation of the sump product yielded 577 g of 3-chloropropyl-trichlorosilane and 132 g of propyltrichlorosilane. This corresponds to 229 g of propyltrichlorosilane, based on 1000 g of 3-chloropropyl-trichlorosilane, and thus an excess consumption of 175 g of trichlorosilane per 1000 g of 3-chloropropyl-trichlorosilane.

Comparative Example 4

The run described in Example 1 was repeated, except that 4.8 mols (552 g) of methylhydrogendichlorosilane and 4.0 mols (306 g) of allyl chloride were used.

The gas chromatogram of the sump product showed that it contained 3-chloropropyl-methyldichlorosilane besides propylmethyldichlorosilane and methylhydrogendichlorosilane.

Distillation of the sump product yielded 519 g of 3-chloropropylmethyldichlorosilane and 68 g of propylmethyldichlorosilane. This corresponds to 131 g of propylemthyldichlorosilane, based on 1000 g of 3-chloropropylmethyldichlorosilane, and thus an excess consumption of 96 g of methyldrogedichlorosilane per 1000 g of 3-chloropropylmethyldichlorosilane.

EXAMPLE 5

The run described in Example 2 was repeated, except that instead of trichlorosilane, 4.0 mols (306 g) of allyl chloride were first introduced into the flask. Ten portions of 55.6 g each (0.41 mol) of trichlorosilane were then added at intervals of 2.7 hours from the dropping funnel. After completion of the reaction, the sump product was gas chromatographically analyzed and worked up by distillation.

The gas chromatogram showed that the sump product contained 3-chloropropyltrichlorosilane besides propyltrichlorosilane and trichlorosilane.

Distillation of the sump product yielded 577 g of 3-chloropropyltrichlorosilane and 7.1 g of propyltrichlorosilane. This corresponds to 12 g of propyltrichlorosilane, based on 1000 g of 3-chloropropyltrichlorosilane, and thus an excess consumption of only 9 g of trichlorosilane per 1000 g of 3-chloropropyltrichlorosilane.

Example 6

The run described in Example 5 was repeated. 4.0 mols (306 g) of allyl chloride were first introduced into the flask, and
then 4.0 mols (542 g) of trichlorosilane were continuously metered into the flask over a period of 24 hours. After termination of the reaction completion time (1 hour), the sump product was gas chromatographically analyzed and worked up by distillation.

The gas chromatogram showed that the sump product contained 3-chloropropyltrichlorosilane in addition to trace amounts of trichlorosilane, allyl chloride and propyltrichlorosilane. Distillation of the sump product yielded 577 g of 3-chloropropyltrichlorosilane.

Example 7

The run described in Example 6 was repeated, except that 4.0 mols (460 g) of methylhydrogendichlorosilane instead of 4.0 mols of trichlorosilane were continuously metered into the 2-liter flask containing 4.0 mols (306 g) of allyl chloride. After termination of the reaction completion time, the sump product was gas chromatographically analyzed and worked up by distillation.

The gas chromatogram showed that the sump product contained 3-chloropropylmethyldichlorosilane besides trace amounts of allyl chloride, methylhydrogendichlorosilane and propylmethyldichlorosilane. Distillation of the sump product yielded 519 g of 3-chloropropylmethyldichlorosilane.

Example 8

The run described in Example 6 was repeated. 4.0 mols (516 of ethylhydrogendichlorosilane instead of 4.0 mols of trichlorosilane were continuously metered into the 2-liter flask containing 4.0 mols (306 g) of allyl chloride. After termination of the reaction completion time, the sump product was gas chromatographically analyzed and worked up by distillation.

The gas chromatogram showed that the sump product contained 3-chloropropylethyldichlorosilane in addition to trace amounts of allyl chloride, ethylhydrogendichlorosilane and propylethyldichlorosilane. Distillation of the sump product yielded 560 g of 3-chloropropylethyldichlorosilane.

Example 9

The run described in Example 6 was repeated, except that 4.0 mols (378 g) of dimethylhydrogenchlorosilane instead of 4.0 mols of trichlorosilane were continuously metered into the 2-liter flask containing 4.0 mols (306 g) of allyl chloride. After termination of the reaction completion time, the sump product was gas chromatographically analyzed and worked up by distillation. The gas chromatogram showed that the sump product contained 3-chloropropyldimethylchlorosilane besides trace amounts of allyl chloride, dimethylhydrogenchlorosilane and dimethylpropylchlorosilane. Distillation of the sump product yielded 465 g of 3-chloropropyldimethylchlorosilane.

Example 10

The run described in Example 6 was repeated, except that only 3.5 mols (474 g) of trichlorosilane instead of 4.0 mols of trichlorosilane were continuously metered into the 2-liter flask which contained 4.0 mols (306 g) of allyl chloride. After termination of the reaction completion time, the sump product was gas chromatographically analyzed and worked up by distillation.

The gas chromatogram showed that the sump product contained 3-chloropropyltrichlorosilane besides allyl chloride. No propyltrichlorosilane was detected. Distillation of the sump product yielded 497 g of 3-chloropropyltrichlorosilane.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. Process for the preparation of a 3-chloropropylsilane from a hydrogensilane and allyl chloride at a temperature which is at least equal to the boiling point of the higher boiling point reactant, by subjecting the reactants to an addition reaction in the presence of a platinum-containing carrier material located above the reactant mixture, conducting the vapors of the reactant mixture to a condenser while bypassing the carrier material, and passing the condensate formed in the condenser through the carrier material by way of a sluice into the boiling reactant mixture, where the condensate formed in the condenser which flows over the carrier material contains a stoichiometric excess of allyl chloride, based on the hydrogen-silane reaction compound.

2. Process according to claim 1, where the condensate contains at least a three-fold molar excess of allyl chloride.

* * * * *

UNITED STATES PATENT AND TRADEMARK OFFICE
CERTIFICATE OF CORRECTION

PATENT NO. : 5,177,236
DATED : January 5, 1993
INVENTOR(S) : Claus-Dietrich Seiler et al It is certified that error appears in the above-identified patent and that said Letters Patent is hereby corrected as shown below:

Col. 4, line 37, "propylemthyldichlorosilane" should read
--propylmethyldichlorosilane--.

Col. 4, line 39, "methyldrogedichlorosilane" should read
--methylhydrogendichlorosilane--.

Signed and Sealed this

Twenty-sixth Day of April, 1994

Attest:

BRUCE LEHMAN

Attesting Officer    Commissioner of Patents and Trademarks